United States Patent [19]

Hayes, Jr. et al.

[11] Patent Number: 4,851,355
[45] Date of Patent: Jul. 25, 1989

[54] HYDROCARBON GROUP-TYPE ANALYZER SYSTEM

[76] Inventors: Paul C. Hayes, Jr., 2135 Springmill Rd., Kettering, Ohio 45440; Steven D. Anderson, 5295 Belle Isle Dr., Dayton, Ohio 45439

[21] Appl. No.: 65,818

[22] Filed: Jun. 5, 1987

[51] Int. Cl.$^4$ .................... G01N 30/02; G01N 33/00
[52] U.S. Cl. .................... 436/140; 436/141; 436/142; 436/161; 422/70
[58] Field of Search ............ 436/139–143, 436/161; 422/70; 210/656

[56] References Cited

U.S. PATENT DOCUMENTS

| | | | |
|---|---|---|---|
| 3,514,262 | 5/1970 | Ayers et al. | 436/139 |
| 3,527,567 | 9/1970 | Philyaw et al. | 436/139 |
| 3,585,002 | 6/1971 | Boys | 436/139 |
| 3,622,276 | 11/1971 | Haahti et al. | 436/139 |
| 3,669,627 | 6/1972 | Mills | 436/139 |
| 4,254,656 | 3/1981 | Sanford et al. | 73/61.1 C |
| 4,341,634 | 7/1982 | Matsushita et al. | 210/656 |
| 4,476,713 | 10/1984 | Alfredson | 73/61.1 C |

OTHER PUBLICATIONS

"Hydrocarbon Group-Type Analysis Via HPLC-DC", Hayes et al., Written Abstract Distributed, May 23, 1986.
"Quantitative Determination of Hydrocarbons, by Structural Group Type via HPLC with Dielectric Constant Detection", Hayes et al., Anal. Chem., 1985, 57, pp. 2094–2098.

Primary Examiner—Barry S. Richman
Assistant Examiner—T. J. Wallen
Attorney, Agent, or Firm—Charles E. Bricker; Donald J. Singer

[57] ABSTRACT

A method of analysis by high performance liquid chromatography is provided for obtaining an analysis of three components, namely acyclic paraffins, cycloparaffins and unsaturates, present in a liquid hydrocarbon mixture. The method comprises introducing a sample of the mixture to be analyzed into an unsaturates-selective column, passing the eluents from the unsaturates-selective column to a second column, eluting the separated components from the second column, detecting the presence of paraffins and naphthenes in the effluent from the second column, eluting the separated components from the unsaturates-selective column, and detecting the presence of unsaturates in the effluent from the unsaturates-selective column. The unsaturates-selective column is a silver-modified ion exchange column. The second column is a slurry packed column packed with a microparticulate material. The detector is a dielectric constant detector.

8 Claims, 2 Drawing Sheets

HYDROCARBON GROUP-TYPE ANALYZER SYSTEM

RIGHTS OF THE GOVERNMENT

The invention described herein may be manufactured and used by or for the Government of the United States for all governmental purposes without the payment of any royalty.

BACKGROUND OF THE INVENTION

This invention relates to chromatography. In particular this invention relates to the high performance liquid chromatographic separation of a liquid hydrocarbon mixture into three components, namely acyclic paraffins, naphthenes and total unsaturates.

Liquid chromatography has been employed to characterize the group composition of crude oils and petroleum products since the beginning of this century. The fluorescent indicator absorption (FIA) method, ASTM D 1319, has served for over 30 years as the official method of the petroleum industry for measuring the paraffinic, olefinic, and aromatic content of gasolines and jet fuels.

High performance liquid chromatography (HPLC) offers many advantages over open column chromatography, not the least of which is speed. However, a severe shortcoming of most HPLC approaches to a hydrocarbon group-type analysis is the difficulty in obtaining accurate response factors applicable to different distillate products. Accuracy is generally compromised when these response factors are used to analyze hydrotreated and hydrocracked materials. Given significant changes in the hydrocarbon distribution within a certain group-type, analytical results will be misleading for such samples because of the variation in response exhibited by most routinely used HPLC detectors.

It is an object of the present invention to provide an analytical method whereby the acyclic paraffins, cycloparaffins and unsaturates, i.e., aromatics plus olefins, in a solution consisting of many kinds of hydrocarbon compounds can be easily and quickly analyzed with high reproducibility and accuracy.

Other objects and advantages of the present invention will be apparent to those skilled in the art.

SUMMARY OF THE INVENTION

In accordance with the present invention there is provided a method of analysis by high performance liquid chromatography for obtaining an analysis of three components, namely acyclic paraffins, cycloparaffins and unsaturates, present in a liquid hydrocarbon mixture which comprises the steps of:
(a) introducing a sample of the mixture to be analyzed into an unsaturates-selective column;
(b) passing the eluent from the unsaturates-selective column to a second column;
(c) eluting the separated components from the second column;
(d) detecting the presence of paraffins and naphthenes in the effluent from the second column;
(e) eluting the separated components from the unsaturates-selective column; and
(f) detecting the presence of unsaturates in the effluent from the unsaturates-selective column.

Alternatively, steps c–d and e–f can be inverted so that the separated components from the unsaturates-selective column are eluted and detected and thereafter, the paraffins and naphthenes from the second column are eluted and detected.

Also provided in accordance with the invention is an apparatus for performing the above-described method of analysis.

DESCRIPTION OF THE PREFERRED EMBODIMENTS

Figure 1:
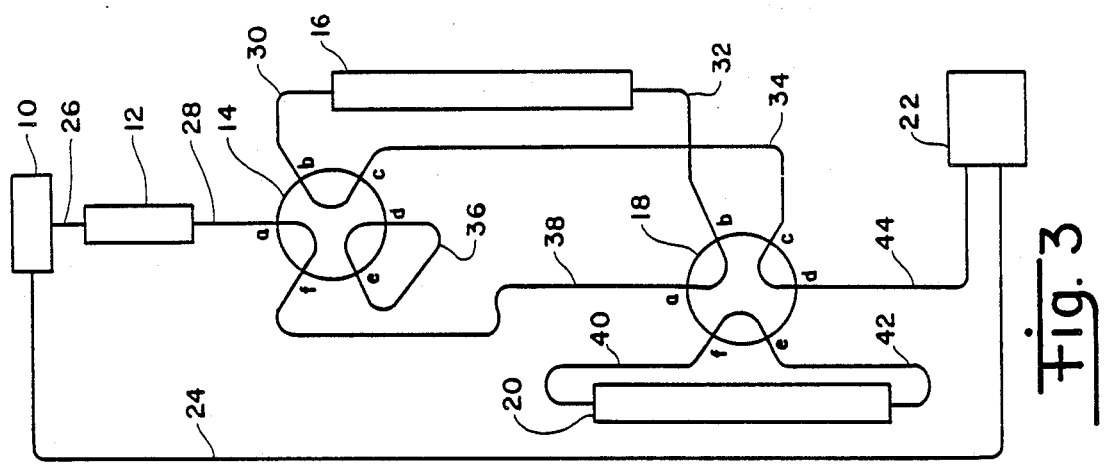
FIGS. 1–3 are schematic diagrams of the chromatographic apparatus of this invention illustrating loading of the columns (FIG. 1), elution and detection of paraffins and naphthenes (FIG. 2) and elution and detection of unsaturates (FIG. 3)

As indicated above, this invention is directed to the separation of hydrocarbon group classes, namely unsaturates, paraffins and naphthenes. According to the invention, petroleum compositions which contain these components can be separated and identified in a rapid and convenient manner using high performance liquid chromatography.

In accordance with the present invention petroleum feed stocks and other products can be separated and analyzed to obtain class separation of paraffins (linear and branched alkanes), naphthenes (cyclic alkanes) and unsaturates (olefins or alkenes and aromatics). The invention is based on the use of an unsaturates-selective column, as hereinafter described, and a slurry packed chromatographic column wherein the column is packed with a microparticulate material having a pore size of less than about 500 and which possesses aromaticity, also described hereinafter.

Petroleum products or hydrocarbon mixtures contain a wide variety of difficult to separate components. A sample of such mixture may contain normal and branched paraffins such as n-hexane, methyl pentane, trimethyl pentane, dimethyl hexane, nonane, dodecane, pentadecane, iso-octane, 2,2,3-trimethyl butane, hendecane and the like. Naphthenes whcih may be present include the cycloaliphatics such as cyclopentane, cyclohexane, cyclooctane methyclohexane, decalins, and the like. Unsaturates which may be present include the C5 to C10 series of mono-olefins, as well as diolefins and isomeric derivatives, and aromatics such as benzene, toluene, the xylenes, the cymenes, and alkyl-substituted derivatives. Obviously, because of close boiling points and close molecular weights in many cases, separation of such mixtures is difficult with any degree of rapidity and economy.

The unsaturates-selective column is a silver-modified ion exchange column. The column is prepared by treating a column having a suitable support and a cation exchange resin bonded phase with silver nitrate. A suitable commercially available column is the Partisil SCX column, available from Whatman, Inc., Clifton, NJ. This column has a silica gel stationary phase and a bonded phase comprising aromatic benzene sulfonic acid functions groups. For use in the present invention, the column is flushed with distilled water and then an aqueous solution of silver nitrate is pumped through the column. The column is then flushed with distilled water until no silver nitrate is detected in the effluent, i.e., generally about 100 ppm silver ion or less. Finally, a suitable water absorber, e.g., dry methanol, acetonitrile, acetone or the like, is pumped through the treated column to remove the water.

The slurry packed column is described by Thomas V. Alfredson, U.S. Pat. No. 4,476,713. Briefly, the column is slurry packed with a microparticulate material which possesses aromaticity and a pore size of less than about 500. A preferred column packing is a commercially available material which comprises polystyrene-divinyl benzene (PS/DVB). This material is a cross-linked polystyrene-divinyl benzene microparticulate support which is available commercially for use in chromatographic columns. In a preferred embodiment the microparticulate material will have a diameter of less than about 20 microns. In a more preferred embodiment the diameter of the microparticulate material will be about 8–10 microns with a pore size of less than about 100. In general, the smaller the diameter of the particulate particle, the higher the efficiency of the column.

The chromatographic column, for both the unsaturates-selective column and the slurry packed column is a stainless steel column of any desired length, but usually being of less than about 100 centimeters.

The microparticulate material is packed in the column as a slurry using any conventional solvent medium. Suitable media for packing the column include alkanes or halogenated alkanes or the like. THe column is preferably packed at low pressure, i.e., less than about 7,000 psi.

Figure 2:
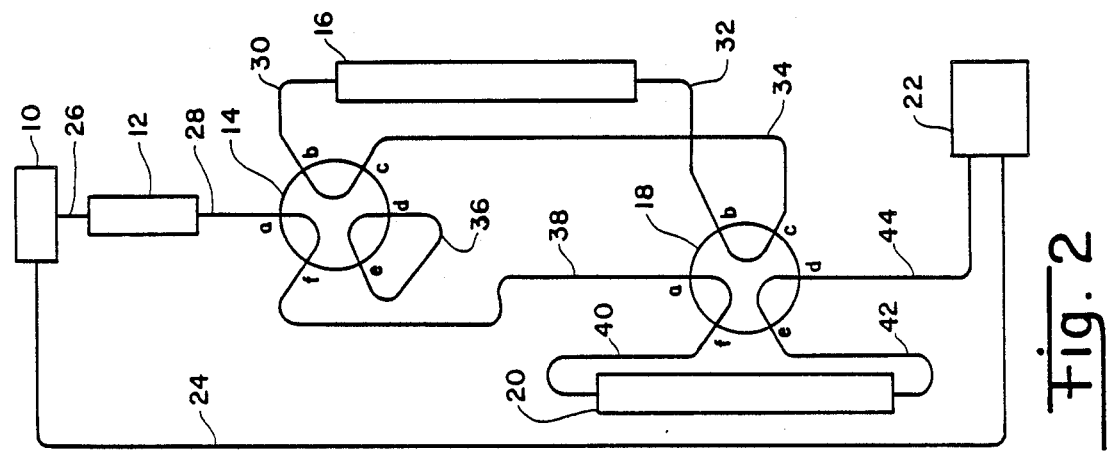
Figure 3:
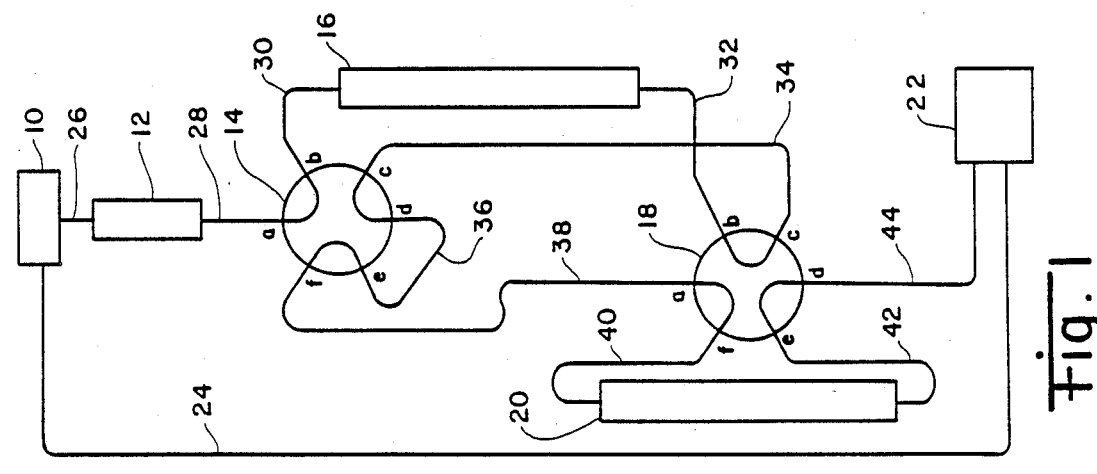

The invention method and apparatus can be understood by reference to FIGS. 1–3, which show in schematic form the method according to a preferred embodiment of the invention. The apparatus shown in FIGS. 1–3 comprises sample injection means 10, an optional guard column 12, 6-way valves 14 and 18, an unsaturates-selective column 16, a slurry packed column 20 and a dielectric constant detector 22, as well as a plurality of conduits connecting various components of the apparatus. Detector 22 provides an output signal in response to a component in a sample. This signal may be to a strip chart recorder or to an integrator, or the like, including combination thereof.

Sample injection means 10 includes reservoirs for the mobile phase fluid and means for introducing the sample into the analyzer and passing the mobile phase through the instrument at a controlled rate, as are well known in the art of liquid chromatography. Sample injection means 10 further includes means for passing a portion of the mobile phase directly to the reference side of detector 22, by way of conduit 24.

Valves 14 and 18 are initially positioned as shown in FIG. 1. In this configuration, material flow proceeds from sample injector means 10 through conduit 26 to guard column 12. The effluent from column 12 is carried by way of conduit 28 to valve 14, thence by way of ports a and b to conduit 30, thence into column 16. The effluent from column 16 is carried by way of conduit 32 to valve 18, thence by way of ports b and c to conduit 34, thence to valve 14, thence by way of ports c and d, closed conduit loop 36 and ports e and f to conduit 38 which carries the material back to valve 18. Material flow continues through ports a and f of valve 18, through conduit 40 to column 20. The effluent from column 20 is carried by way of conduit 42 back through ports e and d of valve 18 thence through conduit 44 to the analysis side of detector 22.

At the beginning of the analysis period, sample injection means 10 is actuated to introduce a predetermined volume of sample into the apparatus. The sample is carried by the mobile phase into and through guard column 12, thence by way of conduit 28, ports a and b of valve 14 and conduit 30 to column 16. After a predetermined period of time $T_1$, valve 14 is repositioned as shown in FIG. 2. Time $T_1$ should be sufficiently long to allow the slowest expected naphthene to elute completely, yet short enough to retain the largest expected unsaturates on column 16. It is presently preferred to base time $T_1$ on the elution times of cis-decalin and n-octylbenzene.

After repositioning of valve 14, it can be seen from FIG. 2 that column 16 is now isolated. The mobile phase is now passed through guard column 12, conduit 28, ports a and f of valve 14, conduit 38, ports a and f of valve 18 and conduit 40 to column 20. Those components which previously eluted through 16 are now separated and eluted through column 20. The effluent from column 20 is passed through conduit 42, ports e and d of valve 18 and conduit 44 to the analysis side of detector 22.

After a suitable time $T_2$, valve 18 is repositioned as shown in FIG. 3. Time $T_2$ may be based on the time required to elute the slowest expected naphthene, e.g., cis-decalin, through column 20; however, it is presently preferred to monitor the output from detector 22 and to reposition valve 18 after the detector output has returned to the base level and remained at that level for a suitable e.g., at least about 1 minute, preferably at least about 4 minutes.

Referring now to FIG. 3, it can be seen that following repositioning of valve 18, column 20 is now isolated and column 16 is set up for backflushing. The mobile phase is now passed through guard column 12, conduit 28, ports a and f of valve 14, conduit 38, ports a and b of valve 18 and conduit 32 to column 16. The effluent from column 16 is passed through conduit 30, ports b and c of valve 14, conduit 34, ports c and d and conduit 44 to the analysis side of detector 22.

Any suitable, substantially non-polar eluent or mobile phase may be utilized. In general, eluents will have a low viscosity, a relatively low solvent strength to enable the chromatographic columns to resolve hydrocarbon groups that characteristically display low capacity factors, and a relatively high dielectric constant to provide uniformity of response in the detector. Suitable eluents include halogen-containing materials such as methylene chloride, 1,1-dichloroethane, n-butyl chloride, and the like, as well as mixed-halogen-containing materials, such as dichlorofluoromethane, chlorodifluoromethane, 2,2-dichloro-1,1,1-trifluoroethane and the like, with 2,2-dichloro-1,1,1-trifluoroethane being preferred.

In the examples which follow, determinations were made using a Varian Model 4200 Liquid Chromatograph (Varian Associates, Walnut Creek, CA) equipped with a Varian Model 8000 autosampler, a six-port injection valve with a 10 microliter sample loop, two six-port backflushing valves, and an Optichrom Model 430 Dielectric Constant Detector (Applied Automation, Inc., Bartlesville, OK) operated at a backpressure of about 1000 psig. A guard column packed with 30–40 micron pellicular silica preceded the analytical columns. Quantitation was accomplished using a Hewlett Packard Model 3357 Laboratory Automation System. The HPLC results are compared to FIA (ASTM D1319)

and mass spectrometric (ASTM D2789) methods. The quantitative results were determined directly in volume percent for each method.

The unsaturates-selective column 16 consisted of a silver nitrate-modified Partisil SCX column (Whatman, Clifton, NJ) 150×4.6 mm ID, 5 μm particle size, prepared as described previously by passing about 25 ml of 1M silver nitrate through a fresh column, flushing with distilled water, and flushing with acetone to remove the water. The slurry-packed column 20 consisted of two Varian Mocropak PONA columns (Varian Associates, Walnut Creek, CA), each 300×7.5 mm ID, packed using Freon 123 (2,2-dichloro-1,1,1-trifluoroethane, Halocarbon Products corp., Hackensack N.J.), in series connection.

Freon 123 was used as the mobile phase. Samples were prepared for analysis by diluting them about 1:15 with Freon 123.

EXAMPLE

A synthetic high density kerosene jet fuel was prepared by blending the following components:

| Hydrocarbon group type | Component | Volume % |
|---|---|---|
| Saturates normal + branched | | |
| | IsoPar C* | 6.0 |
| | Isopar M** | 6.0 |
| cycloparaffins | | |
| | Decalins (cis, trans) | 60.0 |
| | Composite Mixture of $C_8$–$C_{12}$ | 20.0 |
| Aromatics | Composite blend:xylene bottoms ($C_8$–$C_{10}$ benzenes) + tetralin | 8.0 |
| Olefins | | 0.0 |

*isoparaffinic solvent, bp 98–106° C., Exxon, Inc., Houston, TX
**isoparaffinic solvent, bp 207–254° C., Exxon, Inc.

Similarly blended were a standard and a synthetic gasoline. These solutions were analyzed using the apparatus described previously. The results are given in Table I, below.

TABLE I

| Solution | HC Group Type | Volume % Known | Found |
|---|---|---|---|
| Standard | Acyclics | 26.6 | 28.8 |
| | Naphthenes | 24.5 | 22.5 |
| | Aromatics | 48.9 | — |
| | Olefins | 0.0 | — |
| | Total Unsaturates | 48.9 | 48.7 |
| Synthetic Gasoline | Acyclics | 56.0 | 54.4 |
| | Naphthenes | 10.0 | 11.2 |
| | Aromatics | 24.0 | — |
| | Olefins | 10.0 | — |
| | Total Unsaturates | 34.0 | 34.4 |
| Synthetic Kerosene | Acyclics | 12.0 | 12.8 |
| | Naphthenes | 80.0 | 79.0 |
| | Aromatics | 8.0 | — |
| | Olefins | 0.0 | — |
| | Total Unsaturates | 8.0 | 8.2 |

Examination of the above data reveals that the present invention provides accurate results regardless of the carbon number distribution of a particular group type or sample.

A commercial, unleaded gasoline and three kerosene jet fuel samples having widely differing aromatic, olefinic and naphthenic contents were analyzed according to the invention. The results are given in Table II, below. These samples were also analyzed by other techniques. The technique labeled MS in Table II is a standard mass spectrometric method, ASTM D2789, for measuring cycloparaffins, but which had not been calibrated specifically for kerosene samples. The technique labeled LC is the high performance liquid chromatography method given in our co-pending application, Ser. No. 905,413, filed Sept. 9, 1986. The technique labeled FIA is the standard liquid displacement method, ASTM D 1319.

| Sample | Hydrocarbon Group-Type | Volume % Invention | MS | LC | FIA |
|---|---|---|---|---|---|
| Unleaded gasoline | Acyclics | 53.3 | 47.0 | — | — |
| | Naphthenes | 3.6 | 16.7 | — | — |
| | Total saturates | 56.9 | 63.7 | 57.6 | 52.0 |
| | Olefins | — | (10.0) | 11.0 | 10.0 |
| | Aromatics | — | 26.3 | 31.4 | 38.0 |
| | Total unsaturates | 43.1 | 36.3 | 42.4 | 48.0 |
| Kerosene-A | Acyclics | 8.8 | 10.7 | — | — |
| | Naphthenes | 39.6 | 44.9 | — | — |
| | Total saturates | 48.4 | 55.6 | 49.8 | 45.9 |
| | Olefins | — | (0.6) | 0.0 | 0.6 |
| | Aromatics | — | 43.8 | 50.2 | 53.5 |
| | Total unsaturates | 51.6 | 44.4 | 50.2 | 54.1 |
| Kerosene-B | Acyclics | 8.2 | 9.3 | — | — |
| | Naphthenes | 69.0 | 70.6 | — | — |
| | Total saturates | 77.2 | 79.9 | 77.8 | 74.2 |
| | Olefins | — | (0.5) | 0.0 | 0.5 |
| | Aromatics | — | 19.5 | 22.2 | 25.8 |
| | Total unsaturates | 22.8 | 20.0 | 22.2 | 25.8 |
| Kerosene-C | Acyclics | 7.7 | 5.3 | — | — |
| | Naphthenes | 89.0 | 92.1 | — | — |
| | Total saturates | 96.7 | 97.4 | 97.2 | 95.1 |
| | Olefins | — | (0.0) | 0.0 | 0.0 |
| | Aromatics | — | 2.6 | 2.8 | 4.9 |
| | Total unsaturates | 3.3 | 2.6 | 2.8 | 4.9 |

All MS methods can directly analyze only low-olefinic distillates because of an inherent inability to differentiate between olefinic and naphthenic moieties. For those samples containing significant levels of olefins, the standard FIA method is often performed and the olefins found are then subtracted from the appropriate MS data to ascertain total naphthenic content. The data enclosed in parentheses in Table II under the MS column designate olefinic results determined by the FIA. Obviously, any inaccuracies present in the FIA determinations for olefins are thus incorporated into the MS results for cycloparaffins. It is believed that the LC results for total unsaturates are extremely accurate. Note that the results for the method of this invention for total unsaturates closely match the LC results.

Figure 4:
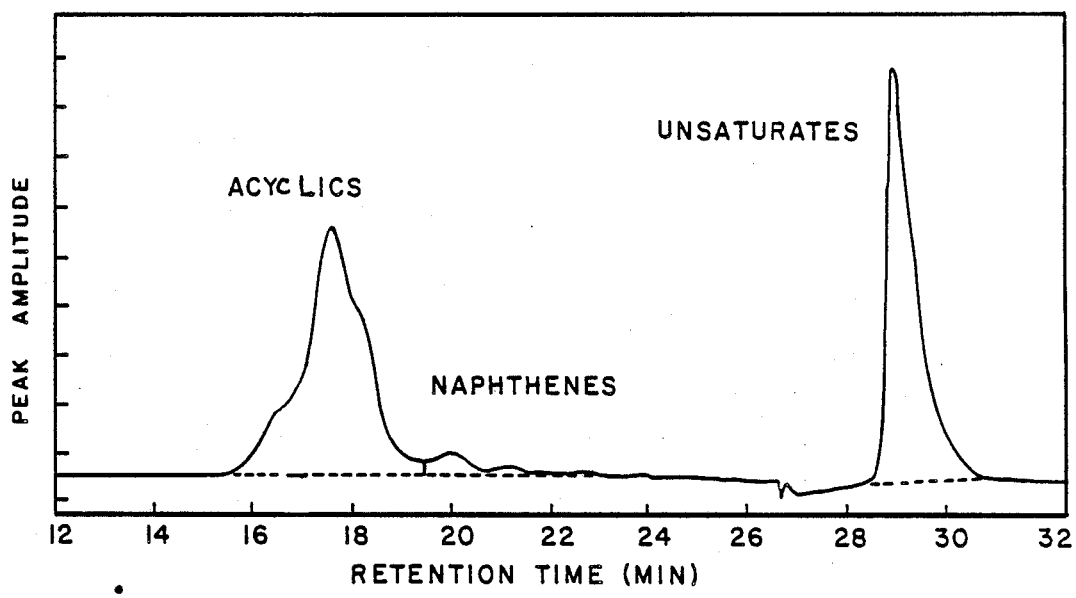
FIG. 4 is a graph of the analysis of a commercial unleaded gasoline in the method of the invention.
Figure 5:
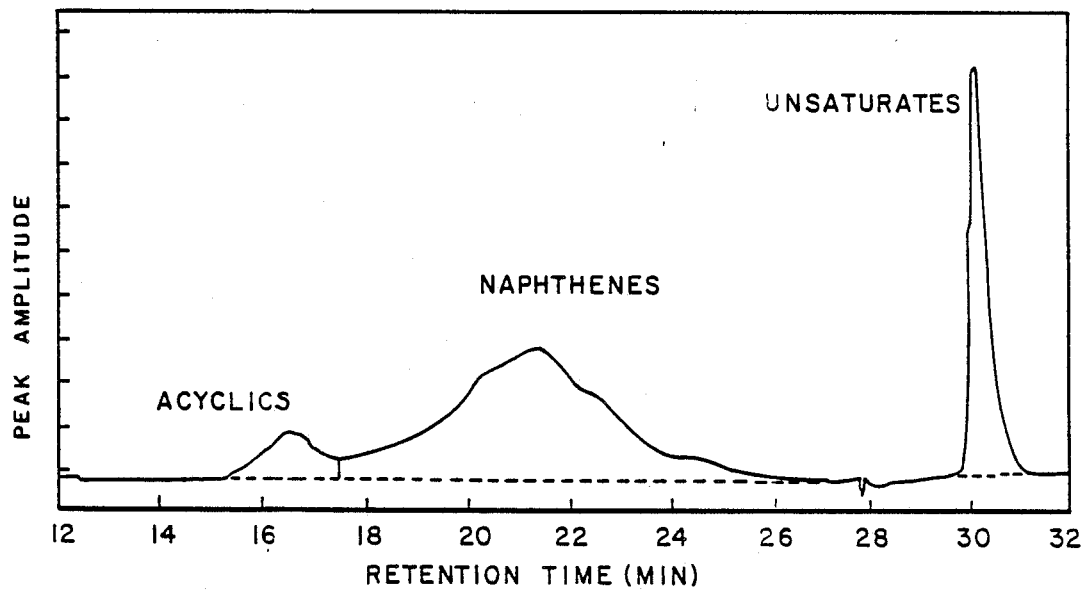
FIG. 5 is a graph of the analysis of a high-density kerosene jet fuel in the method of the invention.

For illustration, the profiles of a commercial unleaded gasoline and a kerosene jet fuel are shown in FIGS. 4 and 5, respectively.

Various modifications may be made without departing from the spirit of the invention or the scope of the appended claims.

We claim:

1. A method for the separation and analysis of paraffins, naphthenes and unsaturates contained in a hydrocarbon mixture which comprises:
   (a) providing a first chromatographic column packed with a particulate material having a silver-modified bonded phase;
   (b) providing at least one second chromatographic column packed with a microparticulate material having a pore size of less than about 500 and possessing aromaticity, said material being slurry packed in a solvent medium;

(c) introducing said hydrocarbon mixture into said first column and passing said mixture therethrough using an eluent selected from the group consisting of methylene chloride, 1,1-dichloroethane, n-butyl chloride, dichlorofluoromethane, chlorodifluoromethane, and 2,2-dichloro-1,1,1-trifluoroethane;

(d) passing the effluent from said first column to said second column;

(e) at a predetermined time $T_1$, isolating said first column and eluting the paraffins and naphthenes through said second column;

(f) detecting the presence of said paraffins and naphthenes in the effluent from said second column;

(g) at a predetermined time $T_2$, isolating said second column and eluting the unsaturates from said first column; and (h) detecting the presence of said unsaturates in the effluent from said first column.

2. The method of claim 1 wherein said paraffins, naphthenes and unsaturates are detected by dielectric constant analysis.

3. The method of claim 1 wherein the microparticulate material in said second column is a polystyrene/divinyl benzene particulate material.

4. The method of claim 3 wherein said microparticulate material has a pore size of less than about 100 and a particle diameter of less than about 20 microns.

5. The method of claim 1 wherein said eluent is 2,2-dichloro-1,1,1-trifluoroethane.

6. The method of claim 1 wherein said bonded phase of said first column comprises aromatic benzene sulfonic acid functional groups.

7. The method of claim 1 wherein said time $T_1$ is based on the elution times of the slowest expanded naphthene and the largest expected unsaturate through said first column, and wherein said time $T_2$ is based upon the elution time of the slowest expected naphthene through said second column.

8. The method of claim 7 wherein said time $T_1$ is based upon the elution times of cis-decalin and n-octylbenzene, and said time $T_2$ is based upon the elution time of cis-decalin.

* * * * *

UNITED STATES PATENT AND TRADEMARK OFFICE
CERTIFICATE OF CORRECTION

PATENT NO. : 4,851,355

DATED : July 25, 1989

INVENTOR(S) : Paul C. Hayes, Jr. et al

It is certified that error appears in the above-identified patent and that said Letters Patent is hereby corrected as shown below:

Col 2, line 44, after "Naphthenes", "whcih" should read "which".

Col 3, line 28, "THe" should read "The".

Col 6, line 28, in the entry line for "Aromatics", the entry under Column "FIA" should read "25.3", instead of "25.8".

Col 8, claim 7, line 2, "expanded" should read "expected".

Signed and Sealed this

Second Day of July, 199

*Attest:*

HARRY F. MANBECK, JR.

*Attesting Officer*     *Commissioner of Patents and Trademarks*